(12) United States Patent
Pan et al.

(10) Patent No.: US 6,390,984 B1
(45) Date of Patent: May 21, 2002

(54) METHOD AND APPARATUS FOR LOCKING SAMPLE VOLUME ONTO MOVING VESSEL IN PULSED DOPPLER ULTRASOUND IMAGING

(75) Inventors: Lihong Pan, Brookfield; Larry Y. L. Mo, Waukesha; Fang Dong, Middleton, all of WI (US); Cynthia Andrews Owen, Memphis, TN (US); Robert S. Stanson, Manitoba (CA); Kjell Kristoffersen, Oslo (NO)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 117 days.

(21) Appl. No.: 09/661,749

(22) Filed: Sep. 14, 2000

(51) Int. Cl.$^7$ .................................................. A61B 8/00
(52) U.S. Cl. ...................................... 600/453; 600/455
(58) Field of Search ................................ 600/453, 455, 600/447; 680/454, 443; 73/625, 628

(56) References Cited

U.S. PATENT DOCUMENTS

| | | | |
|---|---|---|---|
| 4,937,797 A | 6/1990 | Snyder et al. ............... 367/138 |
| 5,365,929 A | 11/1994 | Peterson ................... 128/661.1 |
| 5,690,116 A | 11/1997 | Goujon ................... 128/661.08 |
| 5,942,826 A * | 8/1999 | Even et al. .................. 310/105 |
| 6,068,598 A * | 5/2000 | Pan et al. .................... 600/453 |
| 6,332,509 B1 * | 12/2001 | Nishikawa et al. ......... 181/207 |

FOREIGN PATENT DOCUMENTS

| EP | 0842638 | 5/1998 |
|---|---|---|
| EP | 0985380 | 3/2000 |

* cited by examiner

*Primary Examiner*—Francis J. Jaworski
*Assistant Examiner*—Maulin Patel
(74) *Attorney, Agent, or Firm*—Ostrager Chong & Flaherty LLP

(57) ABSTRACT

A method and an apparatus for automatically maintaining the Doppler sample gate position at a preselected vessel position in B-mode or color flow images during tissue or probe motion. The sample gate is locked onto the selected vessel automatically when the vessel position has changed. Optionally, the vessel slope cursor is automatically updated when the vessel position has changed. The method employs pattern matching of images from successive frames to determine how much a vessel in the image frame has been translated and rotated from one frame to the next. Preferably, either a cross-correlation method is applied to the imaging data in the spatial domain to determine the relative object translation and/or rotation between image frames, or a matched filtering method is applied to the imaging data in the frequency (i.e., Fourier) domain to determine the relative object translation and/or rotation between image frames.

30 Claims, 4 Drawing Sheets

METHOD AND APPARATUS FOR LOCKING SAMPLE VOLUME ONTO MOVING VESSEL IN PULSED DOPPLER ULTRASOUND IMAGING

FIELD OF THE INVENTION

This invention generally relates to the imaging of moving ultrasound scatterers. In particular, the invention relates to methods for positioning the gate or sample volume (hereinafter "sample gate") in medical diagnostic ultrasound imaging.

BACKGROUND OF THE INVENTION

Premium medical diagnostic ultrasound imaging systems require a comprehensive set of imaging modes. These are the major imaging modes used in clinical diagnosis and include timeline Doppler, color flow Doppler, B mode and M mode. In the B mode, such ultrasound imaging systems create two-dimensional images of tissue in which the brightness of a pixel is based on the intensity of the echo return. Alternatively, in a color flow imaging mode, the movement of fluid (e.g., blood) or tissue can be imaged. Measurement of blood flow in the heart and vessels using the Doppler effect is well known. The phase shift of backscattered ultrasound waves may be used to measure the velocity of the backscatterers from tissue or blood. The Doppler shift may be displayed using different colors to represent speed and direction of flow. In the spectral Doppler imaging mode, the power spectrum of these Doppler frequency shifts are computed for visual display as velocity-time waveforms.

One of the primary advantages of Doppler ultrasound is that it can provide noninvasive and quantitative measurements of blood flow in vessels. Given the angle between the insonifying beam and the flow axis (hereinafter referred to as the "Doppler angle"), the magnitude of the velocity vector can be determined by the standard Doppler equation $$v = cf_d/(2f_0 \cos \theta) \quad (1)$$

here c is the speed of sound in blood, $f_o$ is the transmit frequency and $f_d$ is the motion-induced Doppler frequency shift in the backscattered ultrasound signal.

In conventional ultrasound spectral Doppler imaging, the operator is required to manually position the sample gate to the measurement location in a two-dimensional image with or without color flow data. The operator also needs to manually adjust the sample gate size relative to the diameter of the vessel to be studied. From the acoustic data acquired over many transmit firings, Doppler frequency spectral data is obtained via standard Fast Fourier Transform (FFT) spectral analysis.

A two-dimensional B-mode or color (velocity or power) flow image can be used to guide the positioning of the pulsed Doppler sample gate (volume) for blood flow spectral analysis. Color flow is usually used for imaging smaller vessels since it provides a more sensitive detection of weak flow signals. Regardless of whether B-mode or color flow image data is used, it is desirable to be able to maintain the Doppler sample gate at the selected vessel position for, e.g., 10 sec to enable reliable diagnostic waveform index (e.g., systolic to diastolic ratio) calculations.

In practice, however, it is often difficult to keep the sample gate on the vessel of interest due to probe and/or patient motion, including cardiac and breathing. To minimize the associated artifacts or data dropouts, the patient is often asked to hold his or her breath for a number of seconds, which could be difficult for some elderly or sick patients. The sonographer may also try to track vessel motion manually by moving the probe. It should be noted that if color flow imaging is active, the user usually wants to track the moving colorized vessel and not the background B-mode image anatomy. But in practice, it can still be challenging to obtain a good pulsed Doppler sampling of the colorized blood vessels in organs like the kidney because of probe or patient motion.

In spectral Doppler techniques, the angle between the Doppler beam cursor (beam centerline) and the blood vessel orientation (i.e., slope) cursor (i.e., the Doppler angle) is used to convert Doppler frequency shift into velocity units according to Eq. (1). If the Doppler angle changes due to vessel movements, it needs to be updated for correct velocity calculation.

U.S. Pat. No. 5,365,929 describes the use of multiple range gates and multiple Doppler beams to scan a region of interest. By comparing some signal characteristic, such as total power or maximum velocity, of the multiple sample volumes, the scanner automatically selects the best sample gate for full spectral analysis and display. It will appear to the user that the scanner has automatically positioned the sample gate at a location where the Doppler signal is optimal in some sense. The main difficulty with this approach, however, lies in the definition of the signal characteristic for ranking the multiple sample volumes. The obvious choices are signal power or velocity, but, for example, it is quite possible that the user may want to study a diseased portion of the vessel which generates neither the strongest nor the highest velocity signal. Also, in duplex Doppler exams, color data is not available.

European Patent Application No. 0 842 638 A2 describes a method of tracking vessel walls in the B-mode image, and then automatically adjusting the sample volume size to ensure the entire vessel diameter is always covered for volume flow estimation. The vessel wall tracking is based on edge detection algorithms which may work well if the vessel is relatively large with clearly defined walls, and provided that the center of the sample volume remains inside the two walls from frame to frame.

European Patent Application No. 0 985 380 A1 describes a method for automatic positioning of the Doppler sample gate based on bloodstream or color flow information. Among various specific applications, this method can be used to automatically set the sample gate cursor at an optimal position when the sample gate is first brought up in the image, or when it is being moved. The optimal position may be defined by a color flow pixel showing the highest velocity, or the center point of the largest flow segment, or the center point of the next best flow segment, etc. In other words, this invention pertains to selection of an optimal Doppler sampling location within a given color flow image, and not tracking any given vessel from frame to frame.

An automatic method of locking the pulsed Doppler sample gate onto a moving vessel, and updating the Doppler angle when necessary, would clearly facilitate Doppler blood flow studies and/or improve the speed of examination.

SUMMARY OF THE INVENTION

The present invention is directed to a method and an apparatus which automatically keeps the Doppler sample gate at a pre-selected vessel position in B-mode or color flow images during tissue or probe motion. The goal is to lock the sample gate onto the selected vessel automatically when the vessel position has changed. Optionally, the vessel slope cursor is automatically updated when the vessel position has changed. The method employs pattern matching of images from successive frames to determine how much a vessel in the image frame has been translated and rotated from one frame to the next.

In accordance with one preferred embodiment of the invention, a cross-correlation method applied to the imaging data in the spatial domain is used to determine the relative object translation and/or rotation between image frames. In accordance with another preferred embodiment, a matched filtering method is applied to the imaging data in the frequency (i.e., Fourier) domain to determine the relative object translation and/or rotation between image frames. In accordance with a further preferred embodiment, the image registration is performed by combining the spatial and frequency domain methods, e.g., by performing the scaling and rotation registration first using one method and then using the other method to find the x-y translation offsets.

Being a pattern matching technique, the method will work well for B-mode image data that shows clear tissue structures, B-mode flow images, and color flow images. The use of color flow is preferred for smaller vessels (e.g., in the abdomen) which do not show up well in the B-mode image. Another advantage of using color flow is that it can be used directly for vessel segmentation to provide a binary (flow or no flow) image for pattern matching operations.

DETAILED DESCRIPTION OF THE PREFERRED EMBODIMENTS

Figure 1:
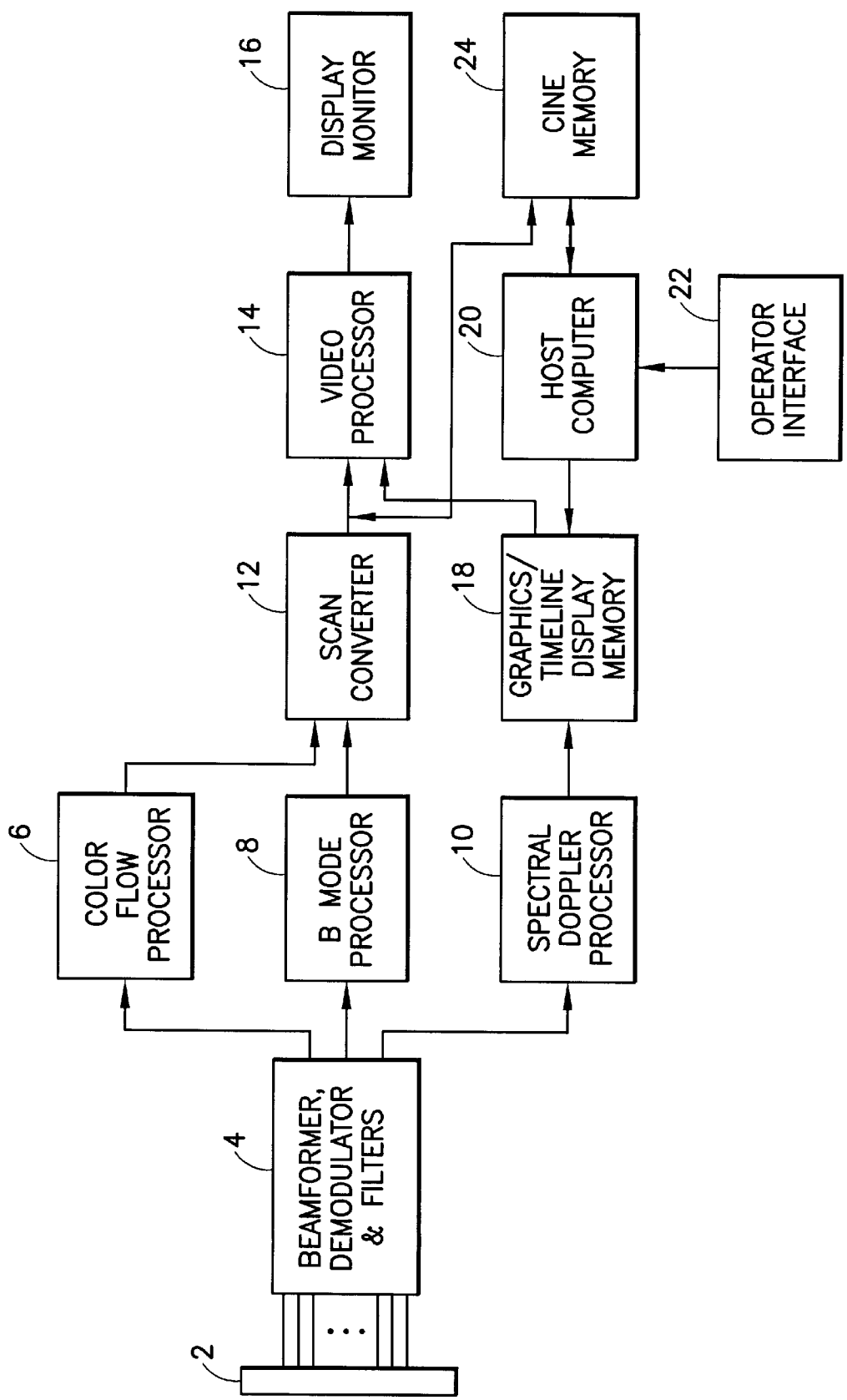
FIG. 1 is a schematic showing a block diagram of a typical ultrasound imaging system which can be programmed with software in accordance with the preferred embodiment of the present invention.

An ultrasound imaging system programmed with software in accordance with the preferred embodiment of the present invention is generally depicted in FIG. 1. The main data path begins with the analog RF inputs to the beamformer board 4 from the transducer 2. The beamformer board 4 is responsible for the transmit and receive beamforming. The beamformer's signal inputs are the low-level analog RF signals from the transducer elements. The beamformer board 4, which comprises a beamformer, a demodulator and filters, outputs two summed digital baseband I and Q receive beams formed from acquired data samples. These data samples are derived from the reflected ultrasound from respective focal zones of the transmitted beams. The I and Q data is sent to FIR filters which are programmed with filter coefficients to pass a band of frequencies centered at the fundamental frequency $f_0$ of the transmit waveform or a (sub)harmonic frequency thereof.

The image data output from the filters is sent to the midprocessor subsystem, where it is processed according to the acquisition mode and output as processed vector data. Typically, the midprocessor subsystem comprises a color flow processor 6, a B-mode processor 8 and a spectral Doppler processor 10. Alternatively, a digital signal processor or array of such processors can be programmed to process signals for all three modes.

The B-mode processor 8 converts the baseband I and Q data from the beamformer board 4 into a log-compressed version of the signal envelope. The B-mode function images the time-varying amplitude of the envelope of the signal as a gray scale. The envelope of a baseband signal is the magnitude of the vector which I and Q represent. The I,Q phase angle is not used in the B-mode display. The magnitude of the signal is the square root of the sum of the squares of the orthogonal components, i.e., $(I^2+Q^2)^{1/2}$. The B-mode intensity data is output to a B-mode acoustic line memory (not shown) in the scan converter 12.

The scan converter 12 accepts the processed B-mode vector data, interpolates where necessary, and converts the data into x-y format for video display. The scan-converted frames are passed to a video processor 14, which maps the video data to a gray-scale mapping for video display. A conventional ultrasound imaging system typically employs a variety of gray maps, which are simple transfer functions of the raw image data to display gray levels. The gray-scale image frames are then sent to the display monitor 16 for display.

The B-mode images displayed by monitor 16 are produced from an image frame of data in which each datum indicates the intensity or brightness of a respective pixel in the display. An image frame may, e.g., comprise a 400×500 data array in which each intensity datum is an 8-bit binary number that indicates pixel brightness. Each pixel has an intensity value which is a function of the backscatter cross section of a respective sample volume in response to interrogating ultrasonic pulses and the gray map employed. The displayed image represents the tissue and/or blood flow in a plane through the body being imaged.

The color flow processor 6 is used to provide a real-time two-dimensional image of blood velocity in the imaging plane. The frequency of sound waves reflecting from the inside of blood vessels, heart cavities, etc. is shifted in proportion to the velocity of the blood cells: positively shifted for cells moving towards the transducer and negatively for those moving away. The blood velocity is calculated by measuring the phase shift from firing to firing at a specific range gate. Instead of measuring the Doppler spectrum at one range gate in the image, mean blood velocity from multiple vector positions and multiple range gates along each vector are calculated, and a two-dimensional image is made from this information. The color flow processor 6 receives the summed left and right, complex I/Q data from the beamformer board 4 and processes it to calculate the mean blood velocity, variance (representing blood turbulence) and total prenormalization power for all sample volumes within an operator-defined region. These three output values are then combined into two final outputs, one primary and one secondary. The primary output will be either velocity or power. The secondary output can be either variance or power. Which two values will be displayed is determined by the operator-selected display mode. Both values are sent to a color acoustic line memory (not shown) in the scan converter 12. The change or shift in backscattered frequency increases when blood flows toward the transducer and decreases when blood flows away from the transducer. Typically, color flow mode displays hundreds of adjacent sample volumes simultaneously, all laid over a B-mode image and color-coded to represent each sample volume's velocity.

In the color flow mode of the conventional ultrasound imaging system, an ultrasound transducer array is activated to transmit a series of multi-cycle (typically 4–8 cycles) tone bursts which are focused at the same transmit focal position with the same transmit characteristics. These tone bursts are fired at a pulse repetition frequency (PRF). The PRF is typically in the kilo-hertz range. A series of transmit firings focused at the same transmit focal position are referred to as a "packet". Each transmit beam propagates through the object being scanned and is reflected by ultrasound scatterers such as blood cells. The return signals are detected by the elements of the transducer array and then formed into a receive beam by a beamformer.

For example, the traditional color firing sequence is a series of firings (e.g., tone bursts) along the same position, which firings produce the respective receive signals:

$$F_1 F_2 F_3 F_4 \ldots F_M$$

where $F_1$ is the receive signal for the i-th firing and M is the number of firings in a packet. These receive signals are loaded into a corner turner memory, and a high pass filter (wall filter) is applied to each down range position across firings, i.e., in "slow time". In the simplest case of a (1, −1) wall filter, each range point is filtered to produce the respective difference signals:

$$(F_1-F_2)(F_2-F_3)(F_3-F_4) \ldots (F_{M-1}-F_M)$$

and these differences are input to a color flow velocity estimator. Typically, the corner turner memory, wall filter and parameter (e.g., velocity) estimators are incorporated into the color flow processor 6.

The color and B-mode acoustic line memories in scan converter 12 respectively accept processed digital data from the color flow and B-mode processors. These components of the scan converter also perform the coordinate transformation of the color flow and B-mode data from polar coordinate (R-θ) sector format or Cartesian coordinate linear format to appropriately scaled Cartesian coordinate display pixel data, which is stored in an X-Y display memory (not shown) in the scan converter. Color flow images are produced by superimposing a color image of the velocity of moving material, such as blood, over a black and white anatomical B-mode image.

If the image to be displayed is a combination of one B-mode frame and one color flow frame, then both frames are passed to the video processor 14, which maps the B-mode data to a gray map and maps the color flow data to a color map for video display. In the final displayed image, the color pixel data is superimposed on the gray-scale pixel data. Successive frames of color flow and/or B-mode data are stored in a cine memory 24 on a first-in, first-out basis. Storage can be continuous or as a result of an external trigger event. The cine memory 24 is like a circular image buffer that runs in the background, capturing image data that is displayed in real time to the user. When the user freezes the system (by operation of an appropriate device on the operator interface 22), the user has the capability to view image data previously captured in cine memory.

In spectral Doppler imaging, the I/Q components are integrated (summed) over a specific time interval and then sampled by the spectral Doppler processor 10. The summing interval and the transmit burst length together define the length of the sample volume (i.e., sample gate) as specified by the user. A "sum and dump" operation effectively yields the Doppler signal backscattered from the sample volume. The Doppler signal is passed through a wall filter which rejects any clutter in the signal corresponding to stationary or very slow-moving tissue. The filtered output is then fed into a spectrum analyzer, which typically takes Fast Fourier Transforms (FFTs) over a moving time window of 32 to 128 samples. Each FFT power spectrum is compressed and then output by the spectral Doppler processor 10 to a graphics/timeline display memory 18. The video processor 14 maps the compressed spectral Doppler data to a gray scale for display on the monitor 16 as a single spectral line at a particular time point in the Doppler velocity (frequency) versus time spectrogram.

System control is centered in a host computer (i.e., master controller) 20, which accepts operator inputs through an operator interface 22 (e.g., a control panel) and in turn controls the various subsystems. The host computer 20 performs system level control functions. It accepts inputs from the operator via the operator interface 22 as well as system status changes (e.g., mode changes) and makes appropriate system changes. A system control bus (not shown) provides the interface from the host computer to the subsystems. A scan controller (not shown) provides real-time (acoustic vector rate) control inputs to the various subsystems. The scan controller is programmed by the host computer with the vector sequences and synchronization options for acoustic frame acquisitions. Thus, the scan controller controls the beam distribution and the beam density. The scan controller transmits the beam parameters defined by the host computer to the subsystems via a scan control bus (not shown).

The conventional system has the capability to superimpose graphical symbols on any ultrasound image. The superimposition of graphics on the image frame is accomplished in the video processor 14, which receives the ultrasound image frame from the X-Y display memory in the scan converter 12 and the graphics data from graphics/timeline display memory 18. The graphics data is processed and input into the graphics/timeline display memory 18 by the host computer 20 or, alternatively, by a dedicated graphics processor which is synchronized with the other subsystems by the host computer. The host computer is programmed to monitor the position of a trackball manipulated by the system operator on the operator interface, acquire spectral Doppler imaging data from a sample volume determined by the trackball position, and superimpose a sample gate cursor on the displayed image frame at a location corresponding to the trackball position. Similarly, the host computer is programmed to monitor the state of a toggle switch on the operator interface and to control the size of the sample volume (and the sample gate cursor) as a function of the state of the toggle switch.

Figure 2:
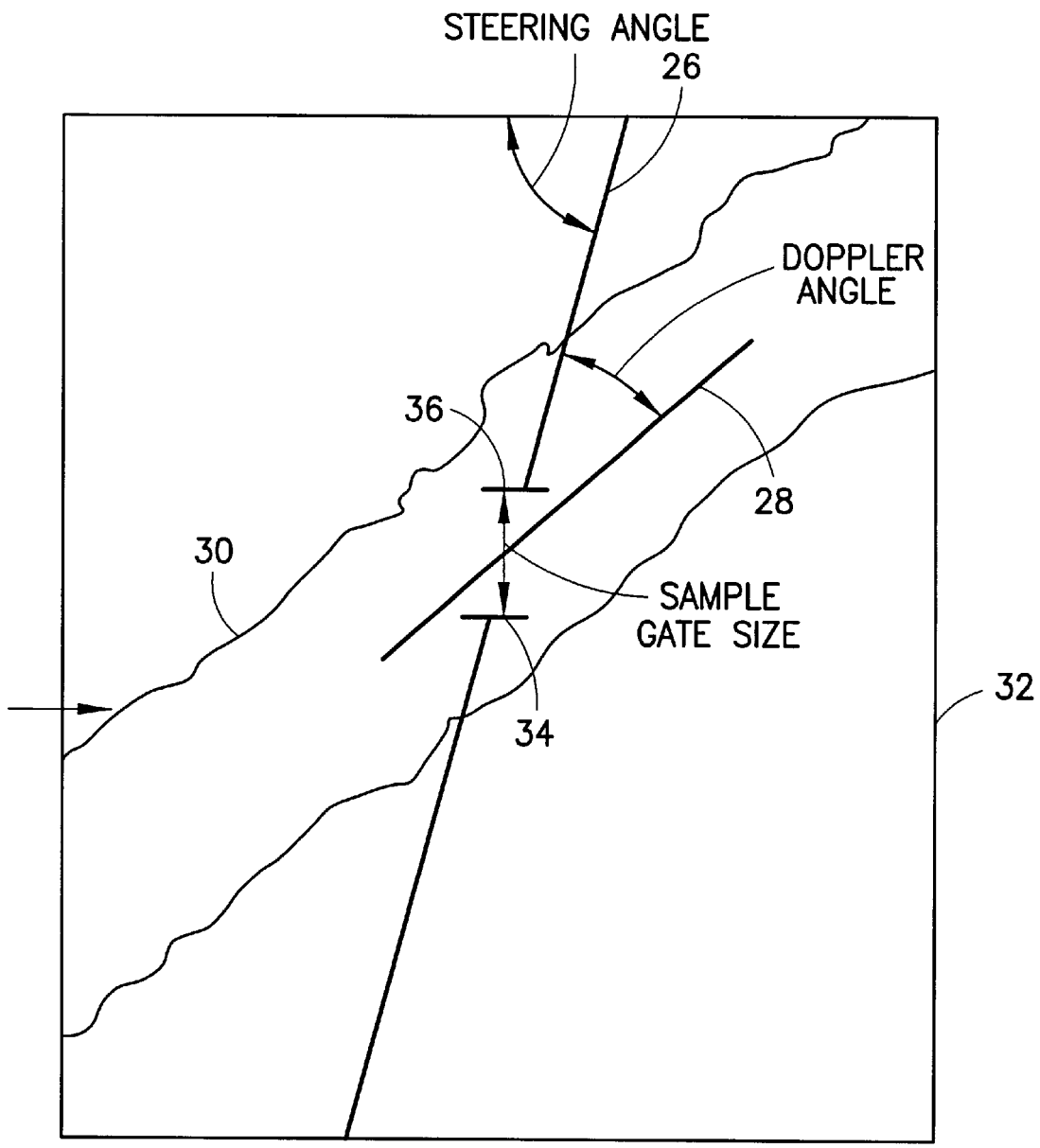
FIG. 2 is a schematic depicting an ultrasound image of a portion of a blood vessel with a sample gate graphic, a Doppler beam cursor and a vessel slope cursor superimposed thereon.

FIG. 2 represents an image frame 32 produced by the system shown in FIG. 1. The exemplary image shown in frame 32 includes a visual representation of a blood vessel 30 with conventional graphics superimposed thereon. The displayed graphics include: a Doppler beam cursor (beam centerline) 26; a vessel slope cursor 28; and a Doppler sample gate (sample volume) cursor, consisting of a sample gate top graphic 36 and a sample gate bottom graphic 34. In the latter type of sample gate cursor, the size of the sample gate is represented by the distance separating the bottom graphic 34 and the top graphic 36 in FIG. 2. However, it will be readily appreciated by persons skilled in the art that the sample gate cursor may have a different geometry, in which case the size of the sample gate would correspond to a dimension of such graphic, e.g., a diameter if the cursor were a circle. The estimated value of the Doppler angle between the Doppler beam cursor 26 and the vessel slope cursor 28 on the vessel 30 in the image 32 is used to convert Doppler frequency shifts into velocity units according to Eq. (1). The Doppler angle value is usually displayed along with the graphic.

Figure 3:
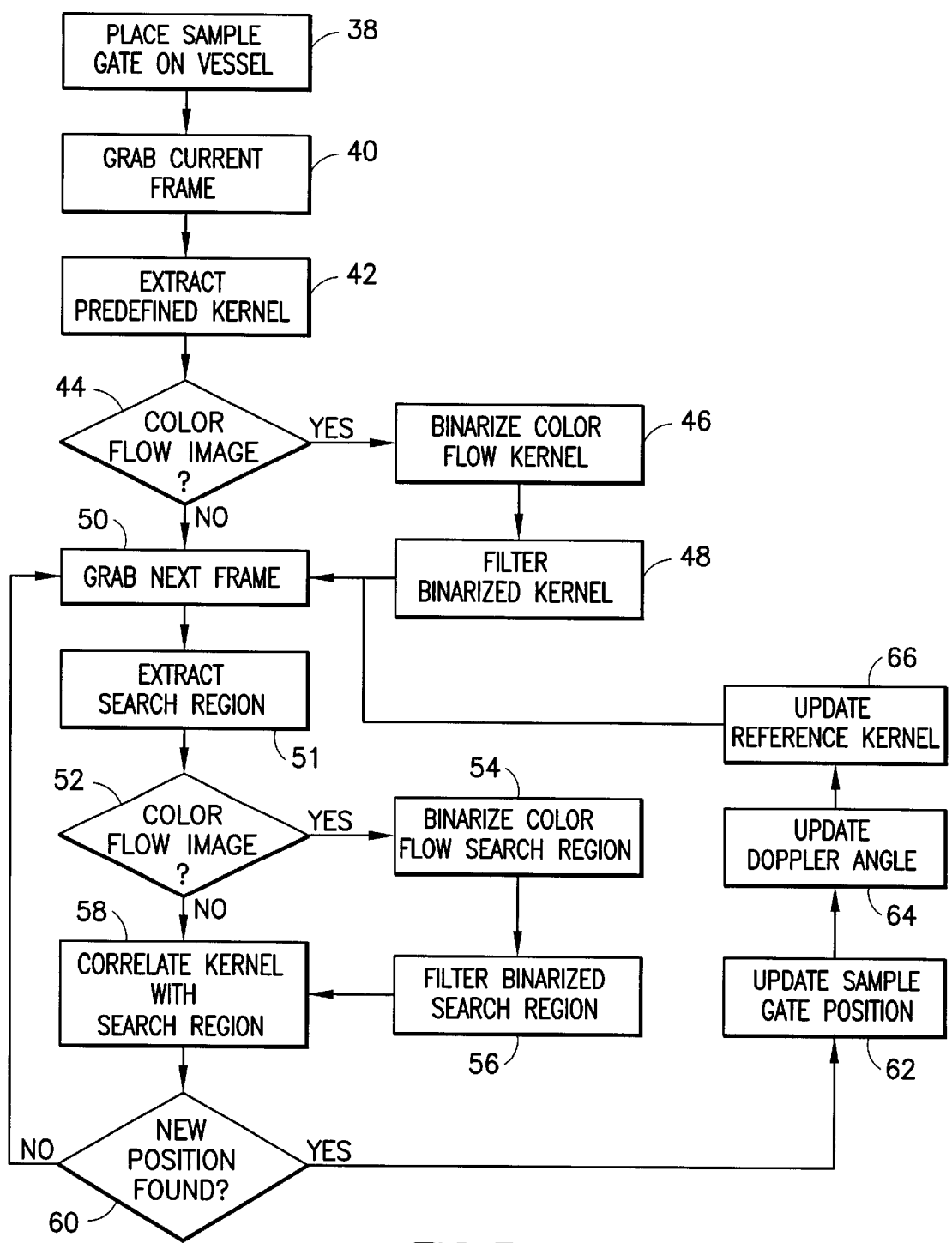
FIG. 3 is a flowchart showing the steps of an algorithm for automatic locking of a pulsed Doppler sample gate onto a moving blood vessel in accordance with the preferred embodiments of the invention.

In accordance with the preferred embodiment of the invention, the position of the sample gate is automatically locked onto a center of a moving blood vessel using a cross-correlation method in the spatial domain and/or a matched filter method in the frequency domain. Referring to FIG. 3, the basic steps of this vessel tracking algorithm are detailed as follows:

First, the sample gate cursor is placed (e.g., via trackball control) at the site of interest within a vessel in a B-mode or color flow image (step 38). Then the current image frame is grabbed from image memory (step 40). The current image frame can be read from either the X-Y display memory in the scan converter (12 in FIG. 1) or the cine memory (24 in FIG. 1). If the current image frame is a color flow (velocity or power) image, RGB or other color pixel formats may be used. A kernel of pixel data, smaller than the image frame and centered around the sample gate position, is extracted from the image frame for analysis (step 42). The kernel size is predefined based on an estimate of the maximum vessel displacement from frame to frame, so the predefined kernel size may vary as a function of image depth and/or the color flow frame rate.

If the image contains color flow data (step 44), the reference kernel of color pixel data is first converted into a binary image (step 46); that is, each pixel is assigned a value of 1 if flow (color) is present and 0 if flow (color) is absent. Optionally, the binarized kernel is subject to one or more passes of morphological filtering (step 48), which should close up most of the small-structure color noises that may be present. In general, the binarized image after adaptive thresholding may be very "noisy," consisting of many small, isolated structures. These small structures (mostly speckle noise) can be eliminated by using morphological filters, which are nonlinear image transformation techniques taught in many digital image processing textbooks (see, e.g., William K. Pratt, Digital Image Processing, 2nd edition, Wiley, N.Y.). Basic morphological operations can be implemented by direct pattern-matching ("hit or miss") transformations, or by using a more efficient pixel stacker and look-up table method. Erosion and dilation represent two basic morphological operations which, when used in series, can be quite effective in closing up the speckle noise structures. Basically, each pass of an erosion filter strips off the outermost pixel layer of a continuous bright ("1") region. This tends to close up the small extraneous bright structures, like speckle noise. The erosion operation will also erode the outermost layer of any blood flow region. To offset this undesirable effect, an opposite operation, called a dilation, can be applied after each pass of an erosion filter. The effect of a dilation filter is to add back a layer of pixels to existing bright objects. Speckle noise gaps which have been completely closed up (no longer exist) by erosion filtering will not be regenerated by the dilation filter. In practice, one pass of the erosion filter followed by a dilation filter can eliminate a majority of speckle noise structures. But if necessary, additional passes of erosion and dilation can be performed.

After the color flow kernel has been binarized, the next color flow image frame is retrieved from memory (step 50). If color flow images are used (step 52), a pre-defined search region in the new image frame is binarized (step 54) and morphologically filtered (step 56) using the previously described technique. Then a spatial cross-correlation (or matched filtering, or combination of both) is performed (58) to register the reference kernel of the first frame within the search region of the second (new) frame. If a registered kernel is found in the search region of the second frame (step 60), then the translation and rotation offsets derived from the offsets are applied to predict or estimate the new vessel position, e.g., the new position of the vessel center, and the sample gate is automatically moved to a new position having a predetermined relationship to a predetermined point on the vessel at the new vessel position (step 62), e.g., the sample gate may be placed at the center of the vessel at the new vessel position. The sample gate cursor on the display screen is moved to a corresponding new position on the displayed image frame. Optionally, the vessel slope and the Doppler angle are recalculated as a function of the new vessel position and an updated vessel slope cursor is displayed (step 64). If the vessel of interest has moved out of the image plane such that no matching structure can be found, the computer returns to step 50 and continues the algorithm from that step. (In this situation, the sonographer may maneuver the probe to bring the vessel back into the image plane, or the vessel may reappear spontaneously at a later time in the cardiac cycle.) After the sample gate position has been updated, the original kernel can remain as reference kernel, or the kernel around the new vessel position becomes the new reference kernel (step 66). The computer then returns to step 50.

On the other hand, if the computer determined in step 44 that color flow data was not present in the first image frame grabbed, then in step 50 the next B-mode image frame is grabbed. The retrieved B-mode image frames then undergo an image registration procedure (step 52) using either cross correlation or matched filtering or a combination of both. The image registration is performed against the reference kernel of pixel data from the first frame and the search region of pixel data from the second frame. If a registered kernel is found in the search region of the second frame (step 60), then the translation and rotation offsets derived from the offsets are applied to predict or estimate the new vessel position, e.g., the new position of the vessel center, and the sample gate is automatically moved to the new vessel position (step 62). The sample gate cursor on the display screen is moved to a corresponding new position on the displayed image frame. Optionally, the vessel slope and the Doppler angle are recalculated as a function of the new vessel position and an updated vessel slope cursor is displayed (step 64).

Regarding step 42, different methods can be used for defining the reference kernel. Even in the absence of translational motion, the diameter of a vessel may vary by 5% or greater over the cardiac cycle. To minimize computation time and maximize the correlation or degree of matching for a selected structure, the kernel size should be chosen to just cover the vessel structure when its diameter is greatest. The vessel dimension (e.g., diameter) can be estimated using standard edge detection methods for ultrasound images. The kernel size can also be varied adaptively under the different noise conditions and vessel structures. In general, the noisier the image, the larger the kernel should be. The tradeoff for the large kernel size is more computation cost and/or reduced sensitivity to small vessels.

Regarding step 58, different well-known methods of image registration can be used. For frame-to-frame correlation in space domain, a computationally efficient algorithm called "SAD" (Sum of Absolute Differences) is taught by Trahey et al. in "Angle independent ultrasonic detection of blood flow," IEEE Trans. Biomedical Engineering, Vol. BME-34, pp. 965–967 (1987). Another effective method is the phase-only matched filtering method in the frequency (Fourier) domain, as detailed below. This is especially efficient for cases which involve non-rigid transformations.

It is possible to perform the image registration by combining the spatial and frequency domain methods. The SAD method may be faster for finding the translation offsets but is less effective when image frames involve scale changes, such as the diameter of the vessel changes under the cardiac cycle. On the other hand, the phase-only matched filter may be more effective in dealing with both scaling and rotation transformations. A composite method could benefit from both methods by performing the scaling and rotation registration first using the phase-only matched filter registration method and then using the SAD algorithm to find the X-Y translation offsets Referring to FIG. 4, a known image registration algorithm using phase-only matched filtering comprises the following steps. The image frame currently retrieved from memory is assigned as the test image g(x, y), and the previous image frame is assigned as the reference image f(x, y), where x and y are the pixel coordinates. Optionally, the test and reference images are both passed through an edge detection block 70. The test and reference images (or edge-detected versions thereof) are sent to be transformed using a two-dimensional Fast Fourier Transform (FFT) 72. The results are the frequency domain representations of two images: G(u, v) and F(u, v). To improve the efficiency of the two-dimensional FFT 42, the test and reference image data can be combined (in an "even location-odd location" separation). Only one two-dimensional FFT is needed to transform both test and reference image data because all the data are real. After the two-dimensional FFT 72, which produces complex data having magnitude and phase, the test and reference image data are decoupled. In step 74, the spectral magnitudes (i.e., absolute values) of both test and reference images are polar-logarithmically transformed into image representations as $g_{pl}(\theta, \lambda)$ and $f_{pl}(\theta, \lambda)$, where is the angle of the polar coordinate system in the frequency domain and $\lambda = \log(\rho)$, where $\rho$ is the radial distance of the polar coordinate system in the frequency domain. After polar-logarithmic transformation in step 74, a two-dimensional FFT is performed (step 76) on the polar-logarithmic representations of the test and reference images, $g_{pl}(\theta, \lambda)$ and $f_{pl}(\theta, \lambda)$. The complex results of step 76, designated $G_{pl}(\xi, \eta)$ and $F_{pl}(\xi, \eta)$, are then operated on by a Fourier phase matching filter 78, which extracts the phase from $G_{pl}(\xi, \eta)$ and from $F_{pl}(\xi, \eta)$, determines the difference between the extracted phases, performs a two-dimensional inverse FFT on that phase difference, searches for the maximum of the result of that two-dimensional inverse FFT, and determines the x, y coordinates of that maximum, namely, $x_{max1}$ and $y_{max1}$. The scaling and rotation parameters are determined from the coordinates of the detected maximum, i.e., the rotation angle $\alpha = \pi(x_{max1}/N_x)$ and the scaling factor $\sigma = e^{(y_{max1}/N_y)}$, where $N_x$ and $N_y$ are the total re-sample numbers along the angular and polar coordinates respectively. The test image in the frequency domain, G(u, v), is then rotated by an angle $-\alpha$ and scaled by a scaling factor $\sigma$ according to the calculated rotation and scaling parameters $\alpha$ and $\sigma$. The test image is re-rotated and re-scaled in the frequency domain instead of the original spatial domain in order to increase the speed of the algorithm. This eliminates one two-dimensional FFT computation, which is very expensive even for a fast CPU or dedicated imaging processor. When the host computer or other signal processing unit performs these rotation and scaling operations, it re-samples the digital image data using some specific interpolation method such as bilinear interpolation. The rotation and scaling are then performed according to the following operation matrix:

$$T = \sigma \begin{bmatrix} \cos\theta & -\sin\theta \\ \sin\theta & \cos\theta \end{bmatrix} \quad (2)$$

where $\sigma$ is the scaling factor and is the rotation angle. The rotation transformation may cause aliasing in the digital image due to the fact that the sampling rate is not high enough for those points far away from the origin of the rotation, and probably too high for those points close to the origin of the rotation. One way to prevent this kind of aliasing is to separate the rotation and scaling matrix T into three consecutive operations:

$$T = \begin{bmatrix} 1 & 0 \\ tg\theta & 1 \end{bmatrix} \begin{bmatrix} \sigma\cos\theta & 0 \\ 0 & \sigma\sec\theta \end{bmatrix} \begin{bmatrix} 1 & tg(-\theta) \\ 0 & 1 \end{bmatrix} \quad (3)$$
$$= H_y(\theta) S(\sigma\cos\theta, \sigma\sec\theta) H_x(-\theta)$$

where $H_x(-\theta)$ is the shear transformation along the x axis; $S(\sigma\cos\theta, \sigma\sec\theta)$ is the scaling along both the x and y axes; and $H_y(\theta)$ is the inverse shear transformation along the y axis. Thus a rotation transformation can be expressed as a sequence of a shear in the x direction, a scaling in both the x and y directions, and an inverse shear in the y direction. These shear and scaling transformations do not introduce any aliasing. Consequently, by separating the transformation matrix T into three basic operations, aliasing can be prevented. These operations are performed by the anti-aliasing rotation and scaling block 80 (see FIG. 4). The output of the anti-aliasing rotation and scaling block 80 is a rotated and scaled frequency domain representation G'(u, v) of the test image. The frequency domain representations F(u, v) and G'(u, v) are then operated on by a Fourier phase matching filter 82, which extracts the phases from F(u, v) and G'(u, v), determines the difference between those extracted phases, performs a two-dimensional inverse FFT on that phase difference, searches for the maximum of the result of that two-dimensional inverse FFT, and then determines the x, y coordinates of that maximum, namely, $x_{max2}$ and $y_{max2}$. The translation parameters are determined from the coordinates of the detected maximum, i.e., the x-axis offset $x_{offset} = x_{max2}$ and the y-axis offset $y_{offset} = y_{max2}$.

In the event that features in consecutive image frames having very little in common (this may be due to the operator moving the probe too fast, causing major anatomical structures in one frame being totally absent in the following frame), the foregoing method will give incorrect rotation, scaling and translation parameters. To assess or predict the correctness of the registration results, the maximum phase difference determined by block 82 is compared to a predetermined threshold, e.g., 0.05, in registration accuracy threshold block 84 (see FIG. 4). If the maximum value is less than the threshold, then the results may not be accurate (indicated by the output labeled NO in FIG. 4). In that event, the current registration parameters should not be used, and the system should ignore the current frame and process the next frame. Alternatively, the system can increase the re-sampling rate in the polar-logarithmic transformation and repeat the algorithm on the current frame until the maximum value of the phase difference exceeds the predetermined threshold.

Figure 4:
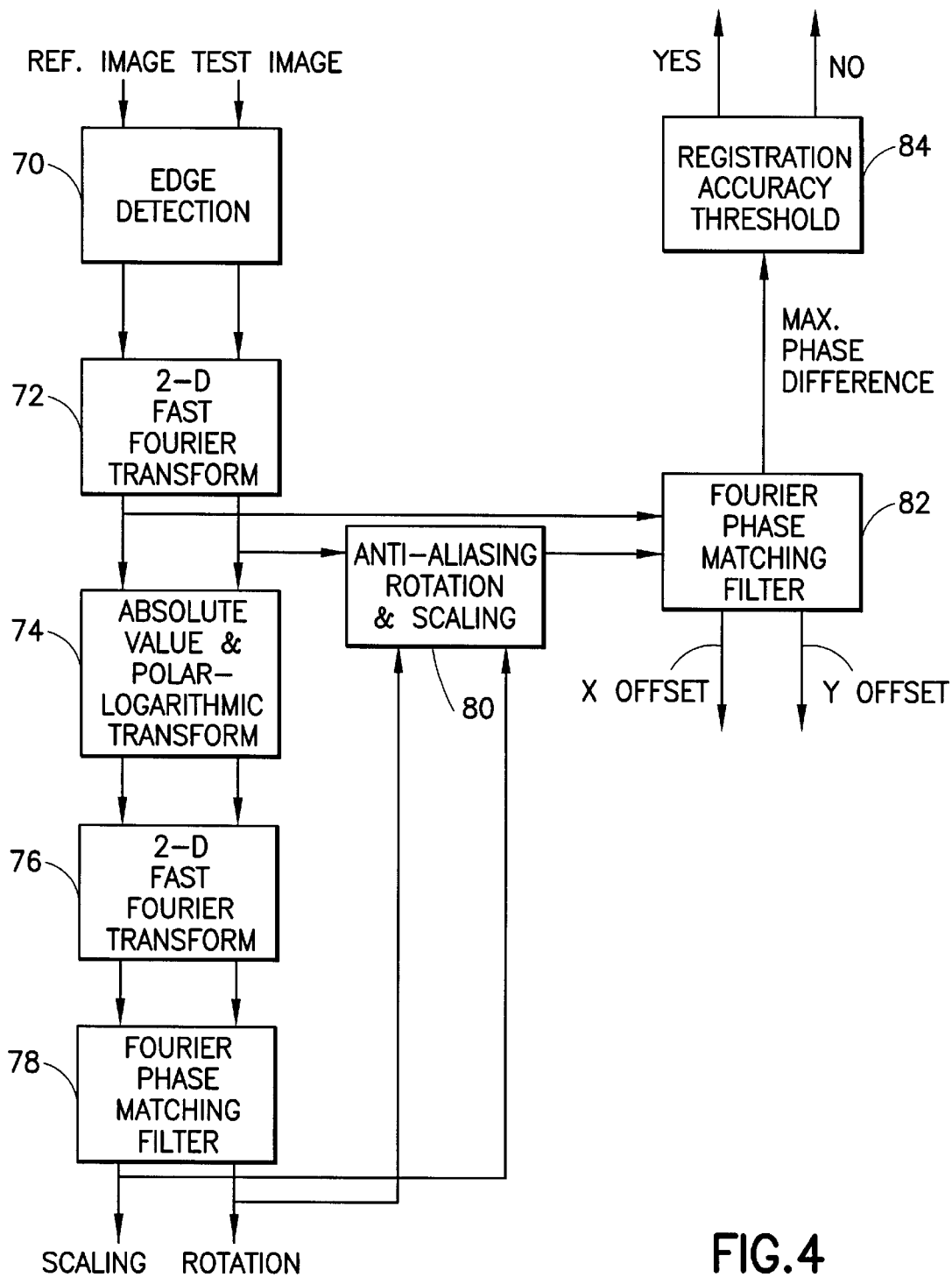
FIG. 4 is a flowchart showing the steps of an image registration algorithm which uses phase-only matched filtering.

If the threshold is exceeded (indicated by the output labeled YES in FIG. 4), the host computer or dedicated processor moves the sample gate cursor in accordance with the calculated parameters to lock the sample gate cursor to the new vessel position. Specifically, translation and rotation offsets derived from the registration are applied to predict the new vessel position. The sample gate cursor is then moved to the new vessel position. The entire process depicted in FIG. 4 is repeated for each new image frame retrieved from memory, enabling automatic locking of the sample gate cursor onto a moving blood vessel.

While the invention has been described with reference to preferred embodiments, it will be understood by those skilled in the art that various changes may be made and equivalents may be substituted for elements thereof without departing from the scope of the invention. In addition, many modifications may be made to adapt a particular situation to the teachings of the invention without departing from the essential scope thereof. Therefore it is intended that the invention not be limited to the particular embodiment disclosed as the best mode contemplated for carrying out this invention, but that the invention will include all embodiments falling within the scope of the appended claims.

What is claimed is:

1. A method of locking a sample gate on a vessel segment in a test subject, comprising the steps of:
   (a) acquiring first and second image frames of image pixel values from said test subject, each of said first and second images frames including image pixel values representing respective images of said vessel segment in said test subject;
   (b) processing said first and second image frames of image pixel values to determine the relative translation and relative rotation of said vessel segment between said first and second image frames;
   (c) estimating a new position of said vessel segment as a function of said relative translation and said relative rotation; and
   (d) moving a spectral Doppler sample gate to a position having a predetermined positional relationship to a predetermined point of said vessel segment at said estimated new position.

2. The method as recited in claim 1, wherein said processing step comprises the step of image registration.

3. The method as recited in claim 2, wherein said image registration step comprises the step of frame-to-frame correlation in a spatial domain.

4. The method as recited in claim 2, wherein said image registration step comprises the step of matched filtering in a frequency domain.

5. The method as recited in claim 1, wherein said processing step comprises the steps of:
   extracting a kernel of image pixel values from said first image frame;
   extracting a search region of image pixel values from said second image frame; and
   searching said search region for a set of image pixel values which match said image pixel values in said kernel.

6. The method as recited in claim 5, wherein said image pixel values are acquired using B-mode imaging.

7. The method as recited in claim 5, wherein said image pixel values are acquired using color flow imaging.

8. The method as recited in claim 7, wherein said processing step further comprises the step of binarizing said extracted color flow image pixel values prior to said searching step.

9. The method as recited in claim 8, wherein said processing step further comprises the step of morphologically filtering said binarized color flow image pixel values.

10. The method as recited in claim 1, further comprising the step of calculating a slope of said vessel segment in said new position.

11. The method as recited in claim 1, further comprising the step of displaying a sample gate graphic superimposed on an image derived from said second image frame of image pixel values, said sample gate graphic being located relative to said vessel segment in accordance with said position to which said sample gate was moved.

12. A system comprising:
   a display device comprising a multiplicity of pixels;
   a memory for storing first and second frames of image pixel values, each of said first and second images frames including image pixel values representing respective images of a vessel segment in a test subject; and
   a computer programmed to perform the steps of:
   (a) controlling said display device to display an image derived from said second frame of image pixel values;
   (b) processing said first and second image frames of image pixel values to determine the relative translation and relative rotation of said vessel segment between said first and second image frames;
   (c) estimating a new position of said vessel segment as a function of said relative translation and said relative rotation; and
   (d) determining the position of a spectral Doppler sample gate relative to a predetermined point in said vessel segment when said vessel segment is at said estimated new position.

13. The system as recited in claim 12, wherein said computer is further programmed to perform the step of controlling said display device to display a sample gate graphic superimposed on said image, said sample gate graphic being located relative to said vessel segment in accordance with said determined position.

14. The system as recited in claim 12, wherein said processing step comprises the step of image registration.

15. The system as recited in claim 14, wherein said image registration step comprises the step of frame-to-frame correlation in a spatial domain.

16. The system as recited in claim 14, wherein said image registration step comprises the step of matched filtering in a frequency domain.

17. The system as recited in claim 12, wherein said processing step comprises the steps of:
   extracting a kernel of image pixel values from said first image frame;
   extracting a search region of image pixel values from said second image frame; and
   searching said search region for a set of image pixel values which match said image pixel values in said kernel.

18. The system as recited in claim 17, wherein said image pixel values comprise B-mode data.

19. The system as recited in claim 17, wherein said image pixel values comprise color flow data.

20. The system as recited in claim 19, wherein said processing step further comprises the step of binarizing said extracted color flow image pixel values prior to said searching step.

21. The system as recited in claim 20, wherein said processing step further comprises the step of morphologically filtering said binarized color flow image pixel values.

22. The system as recited in claim 12, wherein said computer is further programmed to perform the step of calculating a slope of said vessel segment in said new position.

23. The system as recited in claim 12, further comprising:

an ultrasound transducer array comprising a multiplicity of transducer elements;

a transmit beamformer for pulsing selected transducer elements to transmit a series of ultrasound transmit beams in a scan plane;

a receive beamformer coupled to selected transducer elements of said transducer array for acquiring respective receive signals subsequent to respective beam transmits; and a spectral Doppler processor for deriving spectral Doppler data corresponding to said sample gate from said receive signals.

24. A system comprising:

a display device comprising a multiplicity of pixels;

a memory for storing first and second frames of image pixel values, each of said first and second images frames including image pixel values representing respective images of a vessel segment in a test subject;

means for controlling said display device to display an image derived from said second frame of image pixel values;

means for processing said first and second image frames of image pixel values to determine the relative translation and relative rotation of said vessel segment between said first and second image frames;

means for estimating a new position of said vessel segment as a function of said relative translation and said relative rotation; and means for determining the position of a spectral Doppler sample gate relative to a predetermined point in said vessel segment when said vessel segment is at said estimated new position.

25. The system as recited in claim 24, further comprising means for controlling said display device to display a sample gate graphic superimposed on said image, said sample gate graphic being located relative to said vessel segment in accordance with said determined position.

26. The system as recited in claim 24, wherein said processing means comprise:

means for extracting a kernel of image pixel values from said first image frame;

means for extracting a search region of image pixel values from said second image frame; and means for searching said search region for a set of image pixel values which match said image pixel values in said kernel.

27. The system as recited in claim 26, further comprising means for binarizing said extracted image pixel values.

28. The system as recited in claim 27, further comprising means for morphologically filtering said binarized image pixel values.

29. An ultrasound imaging system comprising a computer programmed to perform the following steps:

acquiring first and second image frames of image pixel values containing image pixel values representing a vessel segment in a test subject;

comparing said first and second image frames;

determining translational and rotational offsets of said second image frame relative to said first image frame;

estimating the position of said vessel segment at the time said second image frame was acquired based on said offsets; and acquiring spectral Doppler imaging data at a sample gate which is located as a function of said estimated position of said vessel segment.

30. The ultrasound imaging system as recited in claim 29, wherein said computer is further programmed to cause a sample gate cursor to be superimposed on an image derived from said second frame of image pixel values, said sample gate cursor being positioned as a function of said estimated position of said vessel segment.

* * * * *